United States Patent [19]

Trotto et al.

[11] Patent Number: 5,556,885

[45] Date of Patent: Sep. 17, 1996

[54] N-ARYL- AND N-HETEROARYLHYDRAZONES OF SUBSTITUTED THIOACIDS AND THE S-OXIDES THEREOF AS INSECTICIDAL AND ACARICIDAL AGENTS

[75] Inventors: Susan Trotto, Yardley, Pa.; Joseph A. Furch, III, Lawrenceville, N.J.; David G. Kuhn; David A. Hunt, both of Newtown, Pa.

[73] Assignee: American Cyanamid Company, Madison, N.J.

[21] Appl. No.: 330,047

[22] Filed: Oct. 27, 1994

[51] Int. Cl.⁶ .................... A01N 33/26; C07C 251/80; C07C 245/04; C07C 251/72
[52] U.S. Cl. .................... 514/639; 514/150; 534/567; 534/728; 564/251
[58] Field of Search .................... 564/251; 534/567, 534/728; 514/150, 639

[56] References Cited

U.S. PATENT DOCUMENTS

| | | | |
|---|---|---|---|
| 3,332,936 | 7/1967 | Diekmann | 564/251 X |
| 3,423,409 | 1/1969 | Blatter | 564/251 X |
| 3,424,723 | 1/1969 | Yates et al. | 564/251 X |
| 3,829,492 | 8/1974 | Miller et al. | 564/251 X |
| 3,867,449 | 2/1975 | Moore | 564/251 X |
| 4,621,156 | 11/1986 | Barton et al. | 564/250 |
| 5,246,933 | 9/1993 | Turnbull et al. | 514/249 |

FOREIGN PATENT DOCUMENTS

| | | | |
|---|---|---|---|
| 2038319 | 7/1980 | United Kingdom | C07C 109/04 |

OTHER PUBLICATIONS

Eistert et al., Chemische Berichte, 1963, vol. 96, No. 9, pp. 2290–2303.

Matsubara et al., Chemical and Pharmaceutical Bulletin, 1985, vol. 33, No. 7, pp. 3009–3011.

Bettarini et al., Pesticide Science, 1994, vol. 40, No. 2, p. 145.

Matsubara et al., Chemical Abstracts, 1988, vol. 108, No. 15, abstract #131138x. "The Structure and Reactions of (Phenylhydrazonomethylthio) alkanes" and Nippon Kagaku Kaishi, 1987, No. 7, pp. 1304–1307.

Moon, M. W., Gemrich II, E. G.; Kaugars, G., Journal of Agriculture and Food Chemistry, 20, (4), 888–91 (1972).

Kaugars, G.; Gemrich, II, E. G.; Rizzo, V. L., Journal of Agriculture and Food Chemistry, 21, (4), 647–50 (1973).

Primary Examiner—Floyd D. Higel
Attorney, Agent, or Firm—John W. Hogan, Jr.

[57] ABSTRACT

There are provided N-arylthiohydrazone derivatives of formula I

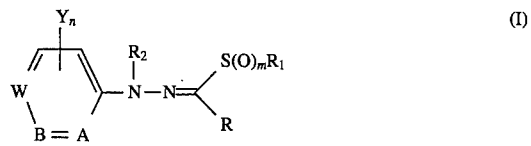

(I)

the use thereof for the control of insect and acarid pests and methods and compositions for the protection of crops from the damage and loss caused by said pests.

20 Claims, No Drawings

N-ARYL- AND N-HETEROARYLHYDRAZONES OF SUBSTITUTED THIOACIDS AND THE S–OXIDES THEREOF AS INSECTICIDAL AND ACARICIDAL AGENTS

BACKGROUND OF THE INVENTION

Significant global economic losses in major agronomic crop production are caused by the damage and infestation of insect and acarid pests. Crop reduction due to said pests, for example in cotton and peanuts, can range as high as 39% and 78%, respectively. Pest infestation can result in lower yields, lower crop quality, reduced consumption, increased perishability, increased risk of disease, higher processing cost, higher transportation cost and increased market prices. Therefore, new and effective insect and acarid control agents and crop protection methods are a continuing global need.

It is an object of this invention to provide N-arylthiohydrazone derivatives which are effective agents for the control of pestiferous insects and acarina.

It is another object of this invention to provide a method for the protection of growing and harvested crops from the harmful and deleterious effects caused by insect and acarid pests.

It is a further object of this invention to provide insecticidal and acaricidal compositions.

SUMMARY OF THE INVENTION

The present invention provides N-arylthiohydrazone compounds of formula I

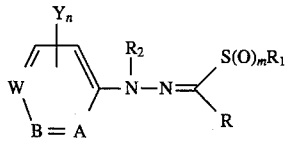

wherein
A is $C-R_3$ or N;
B is $C-R_4$ or N;
W is $C-R_5$ or N with the proviso that at least one of A, B or W must be other than N;
Y is halogen, CN, $NO_2$, $C_1-C_6$alkyl, $C_1-C_6$haloalkyl, $C_1-C_6$alkoxy or $C_1-C_6$haloalkoxy;
n and m are each independently an integer of 0, 1 or 2;
R is hydrogen;
  $C_1-C_{10}$alkyl optionally substituted with one or more halogen, $C_3-C_6$cycloalkyl, $C_1-C_4$alkoxy, $C_1-C_4$haloalkoxy, $(C_1-C_4$-alkyl$)$ $SO_x$, $(C_1-C_4$haloalkyl$)$ $SO_x$, phenyl optionally substituted with one to three halogen, $C_1-C_4$alkyl, $C_1-C_4$haloalkyl, $C_1-C_4$alkoxy, $C_1-C_4$haloalkoxy, $(C_1-C_4$alkyl$)$ $SO_x$, $(C_1-C_4$haloalkyl$)$ $SO_x$, $NO_2$ or CN groups, or
  phenoxy optionally substituted with one to three halogen, $C_1-C_4$alkyl, $C_1-C_4$haloalkyl, $C_1-C_4$alkoxy, $C_1-C_4$haloalkoxy, $(C_1-C_4$alkyl$)SO_x$, $(C_1-C_4$haloalkyl$)SO_x$, $NO_2$ or CN groups;
$C_3-C_{12}$cycloalkyl optionally substituted with one or more halogens, $C_1-C_6$alkyl, $C_1-C_4$haloalkyl, $C_1-C_4$alkoxy, $C_1-C_4$haloalkoxy, $(C_1-C_4$alkyl$)SO_x$, $(C_1-C_4$haloalkyl$)SO_x$,
  phenyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups, or
  phenoxy optionally substituted with one to three halogen, $C_1-C_4$alkyl, $C_1-C_4$haloalkyl, $C_1-C_4$alkoxy, $C_1-C_4$haloalkoxy, $NO_2$ or CN groups; or
  phenyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups with the proviso that when R is phenyl, then m must be an integer of 1 or 2;
$R_1$ is hydrogen; $C_1-C_{10}$alkyl optionally substituted with one or more halogen, hydroxy, $C_1-C_4$alkoxy, $C_1-C_4$haloalkoxy, $(C_1-C_4$alkyl$)SO_x$, $CONR_6R_7$, $CO_2R_8$, $R_9$, $R_{10}$,
  $C_3-C_6$cycloalkyl optionally substituted with one to three halogen, $C_1-C_4$alkyl, $C_1C_4$haloalkyl, $C_1-C_4$alkoxy, $C_1-C_4$haloalkoxy, $NO_2$ or CN groups,
  phenyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups, or
  pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups;
$C_2-C_{10}$alkenyl optionally substituted with one or more halogen, hydroxy, $C_1-C_4$alkoxy, $(C_1-C_4$alkyl$)SO_x$, $CONR_6R_7$, $CO_2R_8$, $R_9$, $R_{10}$,
  $C_3-C_6$cycloalkyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups,
  phenyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups, or
  pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups;
$C_2-C_{10}$alkynyl optionally substituted with one or more halogen, hydroxy, $C_1-C_4$alkoxy, $(C_1-C_4$alkyl$)SO_x$, $CONR_6R_7$, $CO_2R_8$, $R_9$, $R_{10}$,
  $C_3-C_6$cycloalkyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups,
  phenyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups, or
  pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups; or
$C_3-C_{12}$cycloalkyl optionally substituted with one or more halogen, hydroxy, $C_1-C_4$alkoxy, $(C_1-C_4$alkyl$)SO_x$, $CONR_6R_7$, $CO_2R_8$, $R_9$, $R_{10}$,
  $C_3-C_6$cycloalkyl optionally substituted with one to three halogen, $C_1-C_4$alkyl, $C_1-C_4$haloalkyl, $C_1-C_4$alkoxy, $C_1-C_4$haloalkoxy, $NO_2$ or CN groups,
  phenyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups, or
  pyridyl optionally substituted with one or more halogen, $C_1-C_4$alkyl, $C_1-C_4$haloalkyl, $C_1-C_4$alkoxy, $C_1-C_4$haloalkoxy, $NO_2$ or CN groups;
$R_2$ is hydrogen or $C_1-C_4$alkyl;
$R_3$, $R_4$ and $R_5$ are each independently hydrogen, halogen, CN, $NO_2$, $(C_1-C_4$alkyl$)$ $SO_x$, $(C_1-C_4$haloalkyl$)$ $SO_x$, $C_1-C_6$alkyl, $C_1-C_6$haloalkyl, $C_1-C_6$alkoxy, or $C_1-C_6$-haloalkoxy;
$R_6$, $R_7$ and $R_8$ are each independently hydrogen or $C_1-C_4$alkyl;

$R_9$ is $NR_{11}R_{12}$,

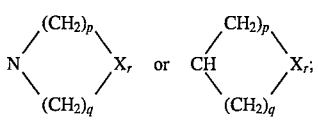

$R_{10}$ is

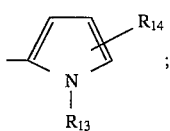

$R_{11}$, $R_{12}$, $R_{13}$ and $R_{14}$ are each independently hydrogen or $C_1$-$C_4$alkyl;

X is O, S or $NR_{13}$;

r is an integer of 0 or 1;

p and q are each independently an integer of 0, 1, 2, or 3 with the proviso that only one of p, q, or r can be 0 and with the further proviso that the sum of p+q+r must be 4, 5 or 6;

x is an integer of 0, 1 or 2; or the acid addition salts thereof. Also provided are methods and compositions for the control of insect and acarid pests and the protection of growing and harvested crops from attack and infestation thereby.

DETAILED DESCRIPTION OF THE INVENTION

A wide variety of insects and acarina cause great economic loss by damaging or destroying agricultural crops and horticultural and pharmaceutical plants; by aiding in the spread and development of bacteria, fungi and viruses that produce diseases of plants; and by destroying or lowering the value of stored foods, other products and possessions. Insect and acarid attack and infestation cause some of the farmers' greatest problems the world over. The need for alternative and effective insect and acarid control is a global concern.

It has now been found that the N-arylthiohydrazone compounds of formula I are highly effective agents for the control of a wide variety of insect and acarid pests.

The formula I thiohydrazone compounds of the present invention have the structural formula

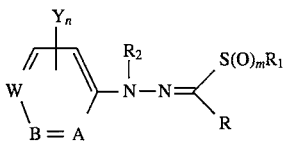

(I)

wherein

A is C-$R_3$ or N;

B is C-$R_4$ or N;

W is C-$R_5$ or N with the proviso that at least one of A, B or W must be other than N;

Y is halogen, CN, $NO_2$, $C_1$-$C_6$alkyl, $C_1$-$C_6$haloalkyl, $C_1$-$C_6$alkoxy or $C_1$-$C_6$haloalkoxy;

n and m are each independently an integer of 0, 1 or 2;

R is hydrogen;

$C_1$-$C_{10}$alkyl optionally substituted with one or more halogen, $C_3$-$C_6$cycloalkyl, $C_1$-$C_4$alkoxy, $C_1$-$C_4$haloalkoxy, ($C_1$-$C_4$-alkyl)$SO_x$, ($C_1$-$C_4$haloalkyl)$SO_x$, phenyl optionally substituted with one to three halogen, $C_1$-$C_4$alkyl, $C_1$-$C_4$haloalkyl, $C_1$-$C_4$alkoxy, $C_1$-$C_4$haloalkoxy, ($C_1$-$C_4$alkyl) $SO_x$, ($C_1$-$C_4$haloalkyl)$SO_x$, $NO_2$ or CN groups, or phenoxy optionally substituted with one to three halogen, $C_1$-$C_4$alkyl, $C_1$-$C_4$haloalkyl, $C_1$-$C_4$alkoxy, $C_1$-$C_4$haloalkoxy, ($C_1$-$C_4$alkyl) $SO_x$, ($C_1$-$C_4$haloalkyl)$SO_x$, $NO_2$ or CN groups;

$C_3$-$C_{12}$cycloalkyl optionally substituted with one or more halogens, $C_1$-$C_6$alkyl, $C_1$-$C_4$haloalkyl, $C_1$-$C_4$alkoxy, $C_1$-$C_4$haloalkoxy, ($C_1$-$C_4$alkyl)$SO_x$, ($C_1$-$C_4$haloalkyl)$SO_x$, phenyl optionally substituted with one to three halogen, $C_1$-$C_4$alkyl $C_1$-$C_4$haloalkyl, $C_1$-$C_4$alkoxy, $C_1$-$C_4$haloalkoxy, $NO_2$ or CN groups, or phenoxy optionally substituted with one to three halogen, $C_1$-$C_4$alkyl, $C_1$-$C_4$haloalkyl, $C_1$-$C_4$alkoxy, $C_1$-$C_4$haloalkoxy, $NO_2$ or CN groups; or phenyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups with the proviso that when R is phenyl, then m must be 1 or 2;

$R_1$ is hydrogen; $C_1$-$C_{10}$alkyl optionally substituted with one or more halogen, hydroxy, $C_1$-$C_4$alkoxy, $C_1$-$C_4$haloalkoxy, ($C_1$-$C_4$alkyl)$SO_x$, $CONR_6R_7$, $CO_2R_8$, $R_9$, $R_{10}$, $C_3$-$C_6$cycloalkyl optionally substituted with one to three halogen, $C_1$-$C_4$alkyl, $C_1C_4$haloalkyl, $C_1$-$C_4$alkoxy, $C_1$-$C_4$haloalkoxy, $NO_2$ or CN groups, phenyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups;

$C_2$-$C_{10}$alkenyl optionally substituted with one or more halogen, hydroxy, $C_1$-$C_4$alkoxy, ($C_1$-$C_4$alkyl)$SO_x$, $CONR_6R_7$, $CO_2R_8$, $R_9$, $R_{10}$, $C_3$-$C_6$cycloalkyl optionally substituted with one to three halogen, $C_1$-$C_4$alkyl, $C_1$-$C_4$haloalkyl, $C_1$-$C_4$alkoxy, $C_1$-$C_4$haloalkoxy, $NO_2$ or CN groups, phenyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups;

$C_2$-$C_{10}$alkynyl optionally substituted with one or more halogen, hydroxy, $C_1$-$C_4$alkoxy, ($C_1$-$C_4$alkyl)$SO_x$, $CONR_6R_7$, $CO_2R_8$, $R_9$, $R_{10}$, $C_3$-$C_6$cycloalkyl optionally substituted with one to three halogen, $C_1$-$C_4$alkyl, $C_1$-$C_4$haloalkyl, $C_1$-$C_4$alkoxy, $C_1$-$C_4$haloalkoxy, $NO_2$ or CN groups, phenyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups; or $C_3$-$C_{12}$cycloalkyl optionally substituted with one or more halogen, hydroxy, $C_1$-$C_4$alkoxy, ($C_1$-$C_4$alkyl)$SO_x$, $CONR_6R_7$, $CO_2R_8$, $R_9$, $R_{10}$, $C_3$-$C_6$cycloalkyl optionally substituted with one to three halogen, $C_1$-$C_4$alkyl, $C_1$-$C_4$halalkyl, $C_1$-$C_4$alkoxy, $C_1$-$C_4$haloalkoxy, $NO_2$ or CN groups, phenyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, or pyridyl optionally substituted with one or more halogen, $C_1$-$C_4$alkyl, $C_1$-$C_4$haloalkyl, $C_1$-$C_4$alkoxy, $C_1$-$C_4$haloalkoxy, $NO_2$ or CN groups;

$R_2$ is hydrogen or $C_1$-$C_4$alkyl;

$R_3$, $R_4$ and $R_5$ are each independently hydrogen, halogen, CN, $NO_2$, $(C_1$-$C_4alkyl)SO_x$, $(C_1$-$C_4haloalkyl)SO_x$, $C_1$-$C_6$alkyl, $C_1$-$C_6$haloalkyl, $C_1$-$C_6$alkoxy, $C_1$-$C_6$haloalkoxy;

$R_6$, $R_7$ and $R_8$ are each independently hydrogen or $C_1$-$C_4$alkyl;

$R_9$ is $NR_{11}R_{12}$,

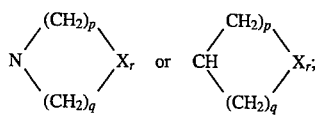

$R_{10}$ is

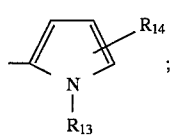

$R_{11}$, $R_{12}$, $R_{13}$ and $R_{14}$ are each independently hydrogen or $C_1$-$C_4$alkyl;

X is O, S or $NR_{13}$;

r is an integer of 0 or 1;

p and q are each independently an integer of 0, 1, 2, or 3 with the proviso that only one of p, q, or r can be 0 and with the further proviso that the sum of p+q+r must be 4, 5 or 6;

x is an integer of 0, 1 or 2; and the acid addition salts thereof.

The term halogen as used in the specification and claims designates chlorine, fluorine, bromine or iodine. The term haloalkyl designates an alkyl group, $C_nH_{2n+1}$ which contains from one halogen atom to 2n+1 halogen atoms. Similarly, the term haloalkoxy designates a $OC_nH_{2n+1}$ group which contains from one to 2n+1 halogen atoms. The halogen atoms may be the same or different. The term acid addition salts designates those salts formed by acids commonly known in the art such as hydrogen chloride, hydrogen bromide, hydrogen bisulfate, hemi-hydrogen sulfate and the like. In the above definition of formula I, when n is an integer of 0 then Y is hydrogen.

Preferred compounds of the invention are those wherein m is 1 or 2; A is C-$R_3$; B is C$R_4$; W is C-$R_5$; Y is halogen and n is 1. More preferred compounds are those wherein m is 1 or 2; R is $C_1$-$C_{10}$alkyl optionally substituted with one or more halogen atoms or $C_3$-$C_6$cycloalkyl optionally substituted with one or more halogen or $C_1$-$C_4$alkyl groups; $R_1$ is $C_1$-$C_6$alkyl optionally substituted with one or more halogen or phenyl groups; $R_3$, $R_4$ and $R_5$ are each independently hydrogen, halogen, $NO_2$ or $C_1$-$C_4$haloalkyl; Y is halogen and n is 1.

Those compounds of formula I wherein m is 1 or 2 may be prepared by the oxidation of the appropriate N-arylthiohydrazone precursor using standard oxidizing reagents such as m-chloroperbenzoic acid (mcpba), hydrogen peroxide and acetic acid, $KMnO_4$ and the like. The reaction is shown in flow diagram I.

Flow Diagram I

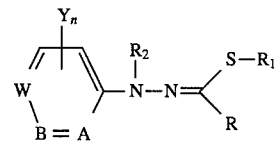

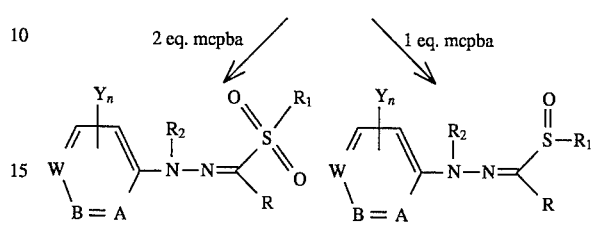

Those compounds of formula I wherein m is 0 may be prepared by reacting the appropriate hydrazinoyl halide of formula II with a suitable mercaptan of formula III in the presence of a base as shown in flow diagram II wherein $X^1$ is halogen.

Flow Diagram II

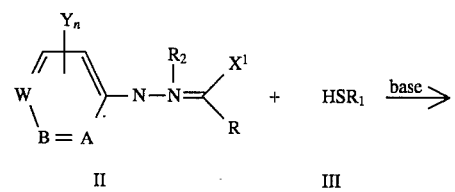

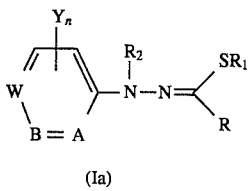

(Ia)

Alternatively, the appropriate N-arylthiohydrazide of formula IV may be reacted with a suitable alkyl or aryl halide of formla V in the presence of a base to give the desired N-arylthiohydrazone compound of formula Ia. The reaction is illustrated flow diagram III.

Flow Diagram III

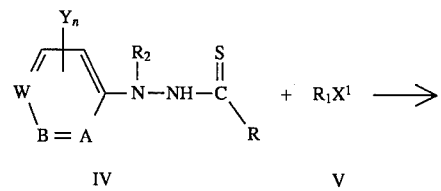

-continued
Flow Diagram III

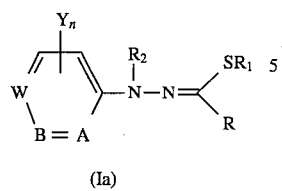

(Ia)

Compounds of formula IV may be readily prepared by those methods known in the art such as that described in U.S. Pat. No. 5,246,933. Compounds of formula Ia may be converted to their S-oxide and S,S-dioxide derivatives as shown hereinabove in flow diagram I.

Growing or harvested crops may be protected from attack or infestation by insect or acarid pests by applying to the foliage of the crops, or to the soil or water in which they are growing, a pesticidally effective amount of a formula I N-arylthiohydrazone derivative.

In actual agronomic practice, generally about 10 ppm to 10,000 ppm, preferably about 100 to 5,000 ppm of the formula I compound dispersed in a liquid carrier, when applied to the plants or the soil or water in which they are growing, is effective to protect the plants from insect and acarina attack and infestation. Applications, such as spray applications, of compositions of the invention are generally effective at rates which provide about 0.125 kg/ha to about 250 kg/ha, preferably about 10 kg/ha to 100 kg/ha of active ingredient. Of course, it is contemplated that higher or lower rates of application of the N-arylthiohydrazone derivatives may be used dependent upon the prevailing environmental circumstances such as population density, degree of infestation, stage of plant growth, soil conditions, weather conditions and the like.

Advantageously, the formula I compounds may be used in conjunction with, or in combination with, other biological and chemical control agents including other insecticides, nematicides, acaricides, molluscicides, fungicides and bactericides such as nuclear polyhedrosis viruses, pyrroles, arylpyrroles, halobenzoylureas, pyrethroids, carbamates, phosphates, and the like.

Typical formulations suitable for the formula I N-arylthiohydrazone derivatives are granular compositions, flowable compositions, wettable powders, dusts, microemulsions, emulsifiable concentrates and the like. All compositions which lend themselves to soil, water and foliage application and provide effective plant protection are suitable. Compositions of the invention include the formula I N-arylthiohydrazone derivative admixed with an inert solid or liquid carrier.

Where compositions of the invention are to be employed in combination treatments with other biological or chemical agents, the composition may be applied as an admixture of the components or may be applied sequentially. While not required, the combination composition comprising a formula I compound and a co-pesticide may also comprise other components, for example, fertilizers, inert formulation aides such as surfactants, emulsifiers, defoamers, dyes, extenders and the like.

In order to aid in the understanding of the invention, specific examples thereof are set forth below. The invention described and claimed herein is not to be limited in scope by these merely illustrative examples. Indeed, various modifications of the invention in addition to those exemplified and described herein will become apparent to those skilled in the art from the following examples and the foregoing description. Such modifications are also intended to fall within the scope of the appended claims. The terms $^1$H, $^{13}$C, $^{19}$FNMR designate proton, carbon and fluorine nuclear magnetic resonance spectroscopy, respectively. IR designates infrared spectroscopy and HPLC designates high performance liquid chromatography.

EXAMPLE 1

Preparation of S-Ethyl-2,2-dimethylthiopropionate, 2-(2,6 dichloro-α,α,α,trifluoro-p-tolyl)hydrazone

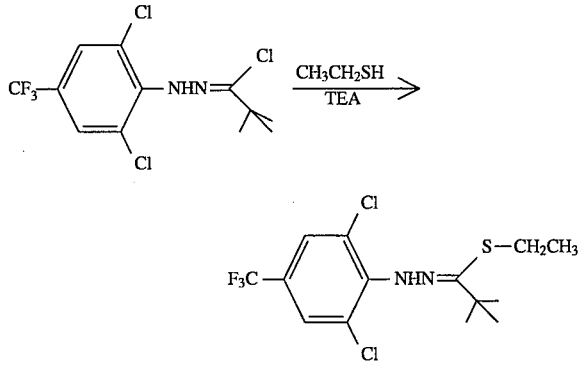

A stirred mixture of ethyl mercaptan (1.6 g, 0.0257 mole) and triethylamine (TEA) (2.87 g, 0.0283 mole) in tetrahydrofuran is treated with a solution of 1-chloro-2,2-dimethylpropionaldehyde, 2-(2,6-dichloro-α,α,α-trifluoro p-tolyl)hydrazone (8.95 g, 0.0257 mole) in tetrahydrofuran at 25° C. When the reaction is complete by thin layer chromatographic analysis, the reaction mixture is poured into water and extracted with ethyl acetate. The combined extracts are dried over sodium sulfate and concentrated in vacuo to give the title product as an orange oil, 8.4 g (87.6% yield), identified by IR, $^1$HNMR, $^{13}$CNMR, $^{19}$FNMR, mass spectral and C, H, N, S, Cl elemental analyses.

EXAMPLE 2

Preparation of S-Methyl-2,2-dimethylthiopropionate, 2-(2,4,6-trichlorophenyl)hydrazone

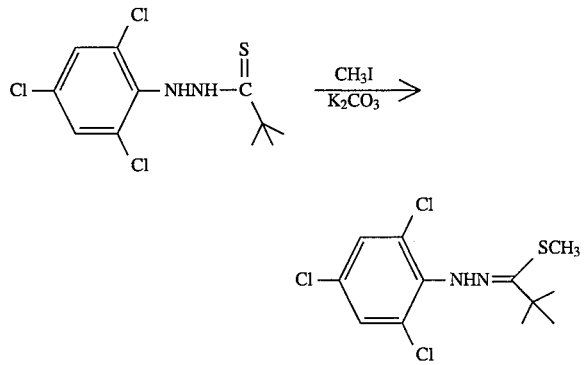

A suspension of 2,2-dimethylthiopropionic acid, 2-(2,4,6-trichlorophenyl)hydrazide (1.37 g, 4.4 mmole) and K$_2$CO$_3$ (0.66 g, 4.8 mmole) is treated dropwise with a solution of methyl iodide (0.684 g, 4.8 mmole) in acetone at reflux temperature, heated at reflux temperature for 2 hours, stirred at room temperature for 18 hours and filtered. The filtrate is concentrated in vacuo to give a brown gum residue. The residue is taken up in ethyl ether, filtered and this filtrate is evaporated to dryness in vacuo to give the title product as a clear red-brown oil, 1.4 g (97.9% yield), identified by IR,

TABLE I $$\text{structure with } W, B=A, Y_n, \text{NHN}=C(SR_1)(R)$$

| Ex. No. | A | B | W | Yn | R | $R_1$ | % Yield |
|---|---|---|---|---|---|---|---|
| 3 | C—Cl | CH | C—CF$_3$ | 6-Cl | —C(CH$_3$)$_3$ | —C$_6$H$_4$pCl | 86.2 |
| 4 | C—Cl | CH | C—CF$_3$ | 6-Cl | —C(CH$_3$)$_3$ | —CH$_2$C$_6$H$_5$ | 69.5 |
| 5 | C—Cl | CH | C—CF$_3$ | 6-Cl | cyclopropyl(CH$_3$)(Cl)(Cl) | —CH$_2$CH$_3$ | 74.1 |
| 6 | C—Cl | CH | C—CF$_3$ | 6-Cl | —C(CH$_3$)$_3$ | —CH(CH$_3$)CH$_2$CH$_3$ | 86.5 |
| 7 | C—Cl | CH | C—CF$_3$ | 6-Cl | —C(CH$_3$)$_3$ | —CH$_2$CH$_2$C$_6$H$_5$ | 66.7 |
| 8 | C—Cl | CH | C—CF$_3$ | 6-Cl | —C(CH$_3$)$_3$ | —CH$_2$CH$_2$CH$_3$ | 82.2 |
| 9 | C—Cl | CH | C—CF$_3$ | 6-Cl | —C(CH$_3$)$_3$ | —CH$_2$(CH$_2$)$_2$CH$_3$ | 65.8 |
| 10* | C—Cl | CH | C—CF$_3$ | 6-Cl | —C(CH$_3$)$_3$ | pyrazinyl | 49.2 |
| 11 | C—Cl | CH | C—CF$_3$ | 6-Cl | —C(CH$_3$)$_3$ | —C(CH$_3$)$_3$ | 76.3 |
| 12 | C—Cl | CH | C—CF$_3$ | 6-Cl | —C(CH$_3$)$_3$ | —CH$_2$C$_6$H$_4$-pCl | 87.0 |
| 13 | C—Cl | CH | C—CF$_3$ | 6-Cl | —C(CH$_3$)$_3$ | —CH$_2$SC(CH$_3$)$_3$ | 88.4 |
| 14 | C—Cl | CH | C—CF$_3$ | 6-Cl | —C(CH$_3$)$_3$ | —CH$_2$COOH$_3$ | 85.7 |
| 15 | C—Cl | CH | C—CF$_3$ | 6-Cl | —C(CH$_3$)$_3$ | —CH(CH$_3$)$_2$ | 80.6 |
| 16 | C—Cl | CH | C—CF$_3$ | 6-Cl | cyclopropyl-C$_6$H$_4$-pCl | —CH$_2$CH$_3$ | 85.5 |
| 17 | C—Cl | CH | C—CF$_3$ | 6-Cl | —C(CH$_3$)$_3$ | —CH$_2$CF$_3$ | 71.1 |
| 18 | C—Cl | CH | C—CF$_3$ | 6-Cl | —C(CH$_3$)$_3$ | —CH$_3$ | 56.5 |
| 19 | C—Cl | CH | C—CF$_3$ | 6-Cl | —C(CH$_3$)$_3$ | —CH$_2$CH=CH$_2$ | — |
| 20 | C—Cl | CH | C—CF$_3$ | 6-Cl | —C(CH$_3$)$_3$ | —CH$_2$-furyl | 82.4 |
| 21 | C—Cl | CH | C—Cl | 6-Cl | —C(CH$_3$)$_3$ | —CH$_2$CH$_2$CF=CF$_2$ | 90.5 |
| 22 | C—Cl | CH | C—CF$_3$ | 6-Cl | —CH(CH$_3$)CH$_2$CH$_3$ | —CH$_3$ | 79.3 |
| 23 | C—Cl | CH | C—CF$_3$ | 6-Cl | —C(CH$_3$)(CH$_2$CH$_3$)(CH$_3$) | —CH$_3$ | 83.1 |
| 24 | C—Cl | CH | C—CF$_3$ | 6-Cl | —CH(CH$_3$)$_2$ | —CH$_3$ | 82.9 |
| 25 | C—Cl | CH | C—CF$_3$ | 6-Cl | —CF$_2$CF$_3$ | —CH$_2$CH$_3$ | 5.0 |
| 26 | C—Cl | CH | C—CF$_3$ | 6-Cl | —CF$_3$ | —CH$_2$CH$_3$ | 76.0 |
| 27 | C—Cl | CH | C—CF$_3$ | 6-Cl | —C(CH$_3$)$_3$ | —CH$_2$CH$_2$N(CH$_3$)$_2$ | 78.2 |

*mp 81°–84° C.

EXAMPLES 3–27

Preparation of N-Arylthiohydrazone Compounds

Using essentially the same procedure described in Examples 1 and 2 and substituting the appropriate reagents, the following compounds shown in Table I are prepared. The compounds obtained are oils, except where indicated, and are identified by $^1$HNMR, $^{13}$CNMR, IR, mass spectral and elemental analyses.

EXAMPLE 28

Preparation of S-Ethyl-2,2-dimethylthiopropionate, 2-(2,6-dichloro-α,α,α-trifluoro-p-tolyl)hydrazone, S-oxide

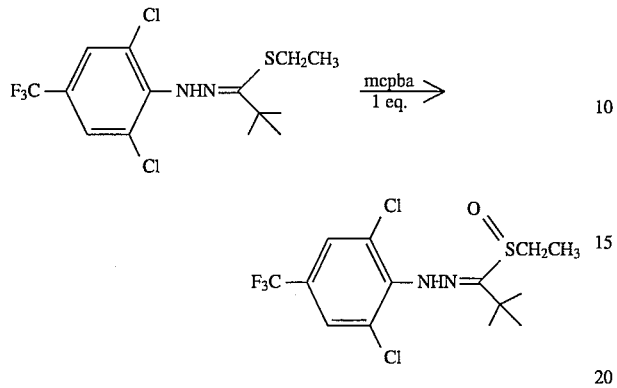

A solution of S-ethyl-2,2-dimethylthiopropionate, 2-(2,6-dichloro-α,α,α-trifluoro-p-tolyl) hydrazone (3.73 g, 0.01 mole) in chloroform is treated incrementally with m-chloroperbenzoic acid (mcpba) (2.88 g of 60 % pure, 0.01 mole) at −10° to −20° C., maintained at −10° C. for 1 hour, warmed to room temperature and filtered. The filtrate is concentrated in vacuo to give a solid residue. Flash column chromatography of the residue using silica-gel; hexanes, followed by 95: 5 hexanes: ethyl acetate as eluent, gives the title product as a straw-yellow oil, in 77.1% yield, identified by IR, $^1$HNMR, $^{13}$FNMR, mass spectral and C, H, N, Cl, F, S elemental analyses.

EXAMPLES 29–33

Preparation of N-Arylthiohydrazone, S-oxide Compounds

Using essentially the same procedure described in Example 28 and substituting the appropriate N-arylthiohydrazone substrate, the following compounds shown in Table II are prepared. The compounds obtained are oils, except where indicated, and are identified by $^1$HNMR, $^{13}$CNMR, IR, mass spectral and elemental analyses.

EXAMPLE 34

Preparation of S-Ethyl-2,2-dimethylthiopropionate, 2-(2,6-dichloro-α,α,α-trifluoro-p-tolyl)hydrazone, S,S-dioxide

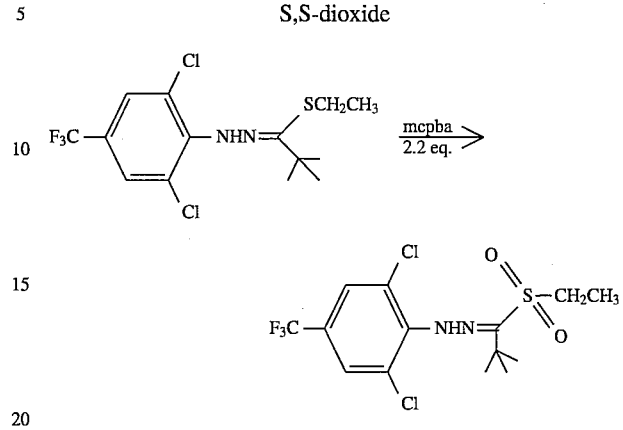

A solution of S-Ethyl-2,2-dimethylthiopropionate, 2-(2, 6-dichloro-α,α,α-trifluoro-p-tolyl)hydrazone (3.73 g, 0.01 mole) and m-chloroperbenzoic acid (mcpba) (6.3 g of 60% pure, 0.022 mole) in tetrahydrofuran is stirred at 25° C. for 3 hours, (reaction is complete by thin layer chromatographic analysis) and poured onto water. The resultant mixture is extracted with ethyl ether. The extracts are combined, washed sequentially with saturated NaHCO$_3$ and water and concentrated in vacuo to give a residue. Flash column chromatography using silica-gel; hexanes gives the title product as a cream-colored solid, in 67.3% yield, mp 98°–101° C., identified by IR, $^1$HNMR, $^{13}$CNMR, $^{19}$FNMR and C, H and N elemental analyses.

EXAMPLES 35–49

Preparation of N-Arylthiohydrazone, S,S-dioxide Compounds

Using essentially the same procedure described in Example 34 and substituting the appropriate N-arylthiohydrazone substrate, the following compounds shown in Table III are prepared. All compounds obtained are identified by $^1$HNMR, $^{13}$CNMR, IR, mass spectral and elemental analyses.

TABLE II

| Ex. No. | A | B | W | Yn | R | R$_1$ | % Yield |
|---|---|---|---|---|---|---|---|
| 29* | C—Cl | CH | C—CF$_3$ | 6-Cl | —C(CH$_3$)$_3$ | —CH$_3$ | 58.1 |
| 30 | C—Cl | CH | C—CF$_3$ | 6-Cl | —C(CH$_3$)$_3$ | —CH(CH$_3$)$_2$ | 72.1 |
| 31* | C—Cl | CH | C—CF$_3$ | 6-Cl | —C(CH$_3$)$_3$ | —CH$_2$CF$_3$ | 22.7 |
| 32* | C—Cl | CH | C—CF$_3$ | 6-Cl | —C(CH$_3$)$_3$ | cyclohexyl | 58.1 |
| 33* | C—Cl | CH | C—CF$_3$ | 6-Cl | —C(CH$_3$)$_3$ | CH$_2$C$_6$H$_5$ | 66.7 |

*Soft Solid
**mp 91°–94°

TABLE III $$\underset{B=A}{\overset{Y_n}{W}} \diagdown \text{NHN} = \underset{R}{\overset{SO_2R_1}{C}}$$

| Ex. No. | A | B | W | Yn | R | R₁ | mp °C. | % Yield |
|---|---|---|---|---|---|---|---|---|
| 35 | C—Cl | CH | C—CF₃ | 6-Cl | —C(CH₃)₃ | —CH₃ | 119.5–121.5 | 29.4 |
| 36 | C—Cl | CH | C—CF₃ | 6-Cl | —C(CH₃)₃ | —CH(CH₃)₂ | oil | 89.4 |
| 37 | C—Cl | CH | C—CF₃ | 6-Cl | —C(CH₃)₃ | cyclohexyl | soft solid | 78.6 |
| 38 | C—Cl | CH | C—CF₃ | 6-Cl | —C(CH₃)₃ | —CH₂C₆H₅ | soft solid | 94.3 |
| 39 | C—Cl | CH | C—CF₃ | 6-Cl | —CF₃ | —CH₂CH₃ | 88.5–90 | 79 |
| 40 | C—Cl | CH | C—CF₃ | 6-Cl | —C(CH₃)₃ | —CH₂-(tetrahydrofuranyl) | soft solid | 58.8 |
| 41 | C—Cl | CH | C—CF₃ | 6-Cl | —C(CH₃)₃ | —CH₂CH=CH₂ | oil | 48.2 |
| 42 | C—Cl | CH | C—Cl | 6-Cl | —C(CH₃)₃ | —CH₃ | soft solid | 94.4 |
| 43 | C—Cl | CH | C—Cl | 6-Cl | —C(CH₃)₃ | —CH₂CH₂CF=CF₂ | soft solid | 23.0 |
| 44 | C—Cl | CH | C—CF₃ | 6-Cl | —C(CH₃)₃ | —C₆H₄-pCl | 89–91 | 30.0 |
| 45 | C—Cl | CH | C—CF₃ | 6-Cl | —C(CH₃)₃ | —C(CH₃)₃ | soft solid | 66.8 |
| 46 | C—Cl | CH | C—CF₃ | 6-Cl | CH₃-(cyclopropyl)-Cl,Cl | —CH₂CH₃ | 70–74 | 91.4 |
| 47 | C—Cl | CH | C—CF₃ | 6-Cl | —C(CH₃)(CH₂CH₃)(CH₃) | —CH₃ | — | 88.7 |
| 48 | C—Cl | CH | C—CF₃ | 6-Cl | —CH(CH₃)(CH₂CH₃) | —CH₃ | oil | 35.7 |
| 49 | C—Cl | CH | C—CF₃ | 6-Cl | —CH(CH₃)₂ | —CH₃ | — | — |

EXAMPLE 50

Insecticidal Evaluation of N-Arylthiohydrazone Compounds

Test solutions are prepared by dissolving the test compound in a 35% acetone in water mixture to give a concentration of 10,000 ppm. Subsequent dilutions are made with water as needed.

Spodoptera eridania, 3rd instar larvae, southern armyworm (SAW)

A Sieva limabean leaf expanded to 7–8 cm in length is dipped in the test solution with agitation for 3 seconds and allowed to dry in a hood. The leaf is then placed in a 100×10 mm petri dish containing a damp filterpaper on the bottom and ten 3rd instar caterpillars. At 5 days, observations are made of mortality, reduced feeding, or any interference with normal molting.

Diabrotic virgifera vergifera Leconte, 3rd instar western corn rootworm (WCR)

One cc of fine talc is placed in a 30 ml wide-mouth screw-top glass jar. One mL of the appropriate acetone test solution is pipetted onto the talc so as to provide 1.25 mg of active ingredient per jar. The jars are set under a gentle air flow until the acetone is evaporated. The dried talc is loosened, 1 cc of millet seed is added to serve as food for the insects and 25 mL of moist soil is added to each jar. The jar is capped and the contents thoroughly mixed on a Vortex Mixer. Following this, ten 3rd instar rootworms are added to each jar and the jars are loosely capped to allow air exchange for the larvae. The treatments are held for 5 days when mortality counts are made. Missing larvae are presumed dead, since they decompose rapidly and can not be found. The concentrations used in this test correspond approximately to 50 kg/ha.

Heliothis virenscens, 3rd instar tobacco budworm (TBW)

Cotton cotyledons are dipped in the test solution and allowed to dry in a hood. When dry, each is cut into quarters and ten sections are placed individually in 30 mL plastic medicine cups containing a 5 to 7 mm long piece of damp dental wick. One 3rd instar caterpillar is added to each cup and a cardboard lid placed on the cup. Treatments are maintained for 3 days before mortality counts and estimates of reduction in feeding damage are made.

The tests are rated according to the scale shown below and the data obtained are shown in Table IV. When more than one test is conducted, the results are averaged.

| RATING SCALE | | | |
|---|---|---|---|
| Rate | % Mortality | Rate | % Mortality |
| 0 | no effect | 5 | 56–65 |
| 1 | 10–25 | 6 | 66–75 |
| 2 | 26–35 | 7 | 76–85 |
| 3 | 36–45 | 8 | 86–99 |
| 4 | 46–55 | 9 | 100 |
|  |  | — | not tested |

TABLE IV

Insecticidal Evaluation Of N-arylthiohydrazone Compounds

| | % Mortality | | | | | |
|---|---|---|---|---|---|---|
| | SAW | | WCR | | TBW | |
| Compound (Ex. No.) | (1000 ppm) | (300 ppm) | (50 ppm) | (10 ppm) | (300 ppm) | (100 ppm) |
| 1 | 9 | 9 | 9 | 9 | 1 | 0 |
| 2 | — | 9 | 9 | 0 | 7 | 3 |
| 3 | 9 | 0 | 0 | 0 | 2 | — |
| 4 | 9 | 9 | 9 | 7 | 9 | 6 |
| 5 | — | 0 | — | — | 0 | 0 |
| 6 | — | 8 | 9 | 0 | 2 | 0 |
| 7 | — | 2 | 6 | 0 | 0 | 0 |
| 8 | — | 9 | 9 | 2 | 6 | 2 |
| 9 | — | 9 | 3 | 1 | 0 | 0 |
| 10 | — | 6 | 0 | — | 0 | 0 |
| 11 | 9 | 9 | 5 | 5 | — | — |
| 12 | — | 9 | 9 | 0 | 9 | 0 |
| 13 | — | 9 | 0 | 0 | 5 | 0 |
| 14 | — | 9 | 8 | 1 | 8 | 0 |
| 15 | — | 9 | 9 | 9 | 9 | 0 |
| 16 | 9 | 0 | 0 | 0 | — | — |
| 17 | 9 | 9 | 9 | 0 | 9 | 9 |
| 18 | 9 | 9 | 9 | 9 | 9 | 0 |
| 19 | 9 | 9 | 9 | 7 | 7 | 0 |
| 20 | 9 | 9 | 5 | 0 | — | — |
| 21 | — | 0 | 0 | 0 | 3 | 0 |
| 25 | 7 | — | 9 | — | — | — |
| 26 | 0 | — | 9 | 2 | — | — |
| 27 | 9 | 5 | 4 | — | 8 | 0 |

EXAMPLE 51

Insecticidal And Acaricidal Evaluation Of N-Arylthiohydrazone, S-Oxide Compounds Test solutions are prepared by dissolving the test compound in a 35% acetone in water mixture to give a concentration of 10,000 ppm. Subsequent dilutions are made with water as needed.

*Tetranychus urticae*(OP-resistant strain), 2-spotted spider mite (TSM)

Sieva limabean plants with primary leaves expanded to 7–8 cm are selected and cut back to one plant per pot. A small piece is cut back to one plant per pot. A small piece is cut from an infested leaf taken from the main colony and placed on each leaf of the test plants. This is done about 2 hours before treatment to allow the mites to move over to the test plant to lay eggs. The size of the cut, infested leaf is varied to obtain about 100 mites per leaf. At the time of test treatment, the piece of leaf used to transfer the mites is removed and discarded. The newly mite-infested plants are dipped in the test solution for 3 seconds with agitation and set in the hood to dry. After 2 days, one leaf is removed and mortality counts are made. After 5 days, another leaf is removed and observations are made of mortality of the eggs and/or newly emerged nymphs.

*Empoasca abrupta*, adults, western potato leafhopper (LH)

A sieva limabean leaf about 5 cm long is dipped in the test solution for 3 seconds with agitation and placed in a hood to dry. The leaf is placed in a 100×10 mm petri dish containing a moist filter paper on the bottom. About 10 adult leafhoppers are added to each dish and the treatments are kept for 3 days before mortality counts are made.

*Aphis fabae*. mixed instar, bean aphid (BA)

Pots containing single nasturtium plants (Tropaeolum sp.) about 5 cm tall are infested with about 100–200 aphids one day before the test. Each pot is sprayed with the test formulation for 2 revolutions of a 4 rpm turntable in a hood, using a #154 DeVilbiss atomizer. The spray tip is held about 15 cm from the plant and the spray directed so as to give complete coverage of the plants and the aphids. The sprayed pots are set on their sides on white enamel trays and held for 2 days, following which mortality estimates are made.

Employing the procedures described in Example 50 and above, the test compounds are evaluated using the rating system described in Example 50. The data obtained are reported in Table V below. When two or more tests are conducted, the results are averaged.

TABLE V

Insecticidal And Acaricidal Evaluation Of N-Arylthiohydrazone, S-Oxide Compounds

| | % Mortality (ppm) | | | | | | | | | |
|---|---|---|---|---|---|---|---|---|---|---|
| | SAW | | WCR | | TSM | | LH | TBW | | BA |
| Compound (Ex. No.) | 1000 | 300 | 50 | 10 | 300 | 100 | 100 | 300 | 100 | 100 |
| 28 | 9 | 9 | 9 | 9 | 8 | 8 | 9 | 9 | 9 | 0 |
| 29 | 9 | 9 | 9 | 9 | 9 | 9 | 9 | 9 | 9 | 9 |
| 30 | 9 | 9 | 9 | 9 | 8 | 4 | 9 | 9 | 9 | 0 |
| 31 | 9 | 9 | 9 | 9 | 8 | 9 | 9 | 9 | 9 | 0 |
| 32 | 9 | 9 | 9 | 5 | 0 | — | — | — | — | — |
| 33 | 9 | 9 | 9 | 5 | 8 | 8 | 5 | 9 | 9 | 8 |

EXAMPLE 52

Insecticidal And Acaricidal Evaluation Of
N-Arylthiohydrazone, S,S-Dioxide Compounds Following the procedures described in Examples 50 and 51, test compounds are evaluated against a variety of insect and acarid species. The rating system is the same as that described in Example 50. The data obtained are reported in Table VI below. When two or more tests are conducted, the results are averaged.

TABLE VI

Insecticidal And Acaricidal Evaluation Of
N-Arylthiohydrazone, S,S-Dioxide Compounds

| | % Mortality (ppm) | | | | | | | | | |
|---|---|---|---|---|---|---|---|---|---|---|
| | SAW | | WCR | | TSM | | LH | TBW | | BA |
| Compound (Ex. No.) | 1000 | 300 | 50 | 10 | 300 | 100 | 100 | 300 | 100 | 100 |
| 34 | 9 | 9 | 9 | 9 | 9 | 9 | 9 | 9 | 9 | 0 |
| 35 | 9 | 9 | 9 | 9 | 9 | 8 | 0 | 9 | 7 | 8 |
| 36 | — | 9 | 9 | 9 | 9 | 9 | 9 | 9 | 7 | 8 |
| 37 | 9 | 9 | 9 | 8 | 9 | 8 | 6 | 9 | 8 | 0 |
| 38 | 9 | — | 9 | 2 | 9 | — | — | — | — | — |
| 40 | 9 | — | 9 | 0 | 9 | 9 | 9 | 0 | 0 | 0 |
| 41 | 9 | 9 | 9 | 8 | 9 | 7 | 9 | 6 | 0 | |
| 42 | 9 | 9 | 9 | 9 | 9 | 9 | 0 | 6 | 0 | 0 |
| 43 | — | 9 | 9 | 8 | 9 | 8 | 9 | 9 | 6 | 7 |
| 44 | 7 | 1 | 7 | 4 | 4 | 0 | 2 | 0 | 0 | 0 |
| 45 | 9 | 9 | 9 | 7 | 8 | 8 | 9 | 9 | 9 | 0 |

What is claimed is:

1. A method for the control of insect or acarid pests which comprises contacting said pests or their food supply, habitat or breeding grounds with a pesticidally effective amount of a compound having the structure

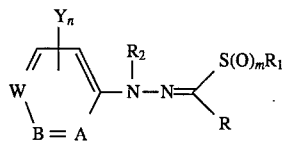

wherein
A is $C-R_3$ or N;
B is $C-R_4$ or N;
W is $C-R_5$ or N with the proviso that at least one of A, B or W must be other than N;
Y is halogen, CN, $NO_2$, $C_1-C_6$alkyl, $C_1-C_6$haloalkyl, $C_1-C_6$alkoxy or $C_1-C_6$ haloalkoxy;
n and m are each independently an integer of 0, 1 or 2;
R is hydrogen; $C_1-C_{10}$alkyl
  unsubstituted or substituted by one or more halogen, $C_3-C_6$cycloalkyl, $C_1-C_4$alkoxy, $C_1-C_4$haloalkoxy, $(C_1-C_4$-alkyl$)SO_x$, $(C_1-C_4$haloalkyl$)SO_x$,
  phenyl unsubstituted or substituted by one to three halogen, $C_1-C_4$alkyl, $C_1-C_4$haloalkyl, $C_1-C_4$alkoxy, $C_1-C_4$haloalkoxy, $(C_1-C_4$alkyl$)SO_x$, $(C_1-C_4$haloalkyl$)SO_x$, $NO_2$ or CN groups, or
  phenoxy unsubstituted or substituted by one to three halogen, $C_1-C_4$alkyl, $C_1-C_4$haloalkyl, $C_1-C_4$alkoxy, $C_1-C_4$haloalkoxy, $(C_1-C_4$alkyl$)SO_x$, $(C_1-C_4$haloalkyl$)SO_x$, $NO_2$ or CN groups;
$C_3-C_{12}$cycloalkyl unsubstituted or substituted by one or more halogens, $C_1-C_6$alkyl, $C_1-C_4$haloalkyl, $C_1-C_4$alkoxy, $C_1-C_4$haloalkoxy, $(C_1-C_4$alkyl$)SO_x$, $(C_1-C_4$haloalkyl$)SO_x$,
  phenyl unsubstituted or substituted by one to three halogen, $C_1-C_4$alkyl $C_1-C_4$haloalkyl, $C_1-C_4$alkoxy, $C_1-C_4$haloalkoxy, $NO_2$ or CN groups, or
  phenoxy unsubstituted or substituted by one to three halogen, $C_1-C_4$alkyl, $C_1-C_4$haloalkyl, $C_1-C_4$alkoxy, $C_1-C_4$haloalkoxy, $NO_2$ or CN groups; or
  phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups with the proviso that when R is phenyl, then m must be 1 or 2;
$R_1$ is hydrogen; $C_1-C_{10}$alkyl unsubstituted or substituted by one or more halogen, hydroxy, $C_1-C_4$alkoxy, $C_1-C_4$haloalkoxy, $(C_1-C_4$alkyl$)SO_x$, $CONR_6R_7$, $CO_2R_8$, $R_9$, $R_{10}$,
  $C_3-C_6$cycloalkyl unsubstituted or substituted by one to three halogen, $C_1-C_4$alkyl, $C_1C_4$haloalkyl, $C_1-C_4$alkoxy, $C_1-C_4$haloalkoxy, $NO_2$ or CN groups,
  phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups, or
  pyridyl unsubstituted or substituted by one or more halogen,
$C_1-C_4$alkyl, $C_1-C_4$haloalkyl, $C_1-C_4$alkoxy, $C_1-C_4$haloalkoxy, $NO_2$ or CN groups;
$C_2-C_{10}$alkenyl unsubstituted or substituted by one or more halogen, hydroxy, $C_1-C_4$alkoxy, $(C_1-C_4$alkyl$)SO_x$, $CONR_6R_7$, $CO_2R_8$, $R_9$, $R_{10}$,
  $C_3-C_6$cycloalkyl unsubstituted or substituted by one to three halogen, $C_1-C_4$alkyl, $C_1-C_4$halo-alkyl, $C_1-C_4$alkoxy, $C_1-C_4$haloalkoxy, $NO_2$ or CN groups,
  phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups, or
  pyridyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups;
$C_2-C_{10}$alkynyl unsubstituted or substituted by one or more halogen, hydroxy, $C_1-C_4$alkoxy, $(C_1-C_4$alkyl$)SO_x$, $CONR_6R_7$, $CO_2R_8$, $R_9$, $R_{10}$,
  $C_3-C_6$cycloalkyl one to three halogen, $C_1-C_4$alkyl, $C_1-C_4$haloalkyl, $C_1-C_4$alkoxy, $C_1-C_4$haloalkoxy, $NO_2$ or CN groups, phenyl unsubstituted or substituted by one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, or pyridyl unsubstituted or substituted by one or more halogen, $C_1$-$C_4$alkyl, $C_1$-$C_4$haloalkyl, $C_1$-$C_4$alkoxy, $C_1$-$C_4$haloalkoxy, $NO_2$ or CN groups; or $C_3$-$C_{12}$cycloalkyl unsubstituted or substituted by one or more halogen, hydroxy, $C_1$-$C_4$alkoxy, $(C_1$-$C_4$alkyl$)SO_x$, $CONR_6R_7$, $CO_2R_8$, $R_9$, $R_{10}$, $C_3$-$C_6$cycloalkyl unsubstituted or substituted by one to three halogen, $C_1$-$C_4$alkyl, $C_1$-$C_4$haloalkyl, $C_1$-$C_4$alkoxy, $C_1$-$C_4$haloalkoxy, $NO_2$ or CN groups, phenyl unsubstituted or substituted by one or more halogen, $C_1$-$C_4$alkyl, $C_1$-$C_4$haloalkyl, $C_1$-$C_4$alkoxy, $C_1$-$C_4$haloalkoxy, $NO_2$ or CN groups, or pyridyl unsubstituted or substituted by one or more halogen, $C_1$-$C_4$alkyl, $C_1$-$C_4$haloalkyl, $C_1$-$C_4$alkoxy, $C_1$-$C_4$haloalkoxy, $NO_2$ or CN groups;

$R_2$ is hydrogen or $C_1$-$C_4$alkyl;

$R_3$, $R_4$ and $R_5$ are each independently hydrogen, halogen, CN, $NO_2$, $(C_1$-$C_4$alkyl$)SO_x$, $(C_1$-$C_4$haloalkyl$)SO_x$, $C_1$-$C_6$alkyl, $C_1$-$C_6$haloalkyl, $C_1$-$C_6$alkoxy or $C_1$-$C_6$haloalkoxy;

$R_6$, $R_7$ and $R_8$ are each independently hydrogen or $C_1$-$C_4$alkyl;

$R_9$ is $NR_{11}R_{12}$,

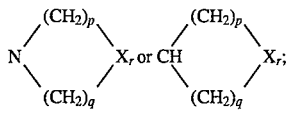

$R_{10}$ is

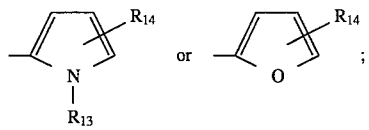

$R_{11}$, $R_{12}$, $R_{13}$ and $R_{14}$ are each independently hydrogen or $C_1$-$C_4$alkyl;

X is O, S or $NR_{13}$;

r is an integer of 0 or 1;

p and q are each independently an integer of 0, 1, 2, or 3 with the proviso the sum of p+q+r must be 4, 5 or 6;

x is an integer of 0, 1 or 2;

the acid addition salts thereof.

2. The method according to claim 1 wherein m is 1 or 2.

3. The method according to claim 1 wherein A is $CR_3$; B is $C$-$R_4$; W is $C$-$R_5$; Y is halogen; n is 1 and $R_2$ is hydrogen.

4. The method according to claim 1 wherein R is $C_1$-$C_{10}$alkyl unsubstituted or substituted by one or more halogen or $C_3$-$C_6$cycloalkyl unsubstituted or substituted by one or more halogen or $C_1$-$C_4$alkyl groups and $R_1$ is $C_1$-$C_{10}$alkyl unsubstituted or substituted by one or more halogen atoms or phenyl groups, $C_2$-$C_{10}$alkenyl unsubstituted or substituted by one or more halogen atoms or phenyl unsubstituted or substituted by one or more halogen atoms.

5. The method according to claim 2 wherein R, $R_1$ and $R_2$ are each independently Hydrogen or $C_1$-$C_{10}$alkyl.

6. The method according to claim 2 wherein A is C-$R_3$; B is C-$R_4$; W is C-$R_5$; Y is halogen; n is 1; $R_2$ is hydrogen and $R_3$, $R_4$, and $R_5$ are each independently hydrogen, halogen or $C_1$-$C_6$haloalkyl.

7. The method according to claim 6 wherein m is 2.

8. The method according to claim 6 wherein the compound is S-ethyl-2,2-dimethylthiopriopionate, 2-(2,6-dichloro-α,α,α-trifluoro-p-tolyl)hydrazone; the S-oxide thereof; the S,S-dioxide thereof or their acid addition salts.

9. A method for the protection of growing plants from attack or infestation by insect or acarid pests which comprises applying to the foliage of the plants, or to the soil or water in which they are growing, a pesticidally effective amount of a compound having the structure

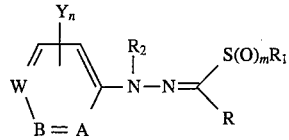

wherein A, B, W, Y, n, R, $R_1$, $R_2$, and m are described in claim 1.

10. The method according to claim 9 wherein m is 1 or 2.

11. The method according to claim 9 wherein A is C-$R_3$; B is C-$R_4$; W is C-$R_5$; Y is halogen; n is 1 and $R_2$ is hydrogen.

12. The method according to claim 10 wherein A is C-$R_3$; B is C-$R_4$; W is C-$R_5$; Y is halogen, n is 1; $R_2$ is hydrogen; $R_3$, $R_4$ and $R_5$ are each independently hydrogen, halogen or $C_1$-$C_6$haloalkyl; $R_{is\ C1}$-$C_{10}$alkyl unsubstituted or substituted by one or more halogen atoms or $C_3$-$C_6$cycloalkyl unsubstituted or substituted by one or more halogen or $C_1$-$C_4$alkyl groups and $R_1$ is $C_1$-$C_{10}$alkyl unsubstituted or substituted by one or more halogen or phenyl groups, $C_2$-$C_{10}$alkenyl unsubstituted or substituted by one or more halogen atoms or phenyl unsubstituted or substituted by one or more halogen atoms.

13. The method according to claim 11 wherein the compound is S-ethyl-2,2-dimethylthiopropionate, 2-(2,6-dichloro-α,α,α-trifluoro-p-tolyl)hydrazone; the S-oxide thereof; the S,S-dioxide thereof or their acid addition salts.

14. A compound having the structure of formula I

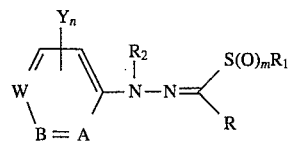

wherein

A is C-$R_3$ or N;

B is C-$R_4$ or N;

W is C-$R_5$ or N with the proviso that at least one of A, B or W must be other than N;

Y is halogen, CN, $NO_2$, $C_1$-$C_6$alkyl, $C_1$-$C_6$haloalkyl, $C_1$-$C_6$alkoxy or $C_1$-$C_6$ haloalkoxy;

n and m are each independently an integer of 0, 1 or 2;

R is $C_1$-$C_{10}$alkyl unsubstituted or substituted by one or more halogen, $C_3$-$C_6$cycloalkyl, $C_1$-$C_4$alkoxy, $C_1$-$C_4$haloalkoxy, $(C_1$-$C_4$-alkyl$)SO_x$, $(C_1$-$C_4$haloalkyl$)SO_x$, phenyl unsubstituted or substituted by one to three halogen, $C_1$-$C_4$alkyl, $C_1$-$C_4$haloalkyl, $C_1$-$C_4$alkoxy, $C_1$-$C_4$haloalkoxy, $(C_1$-$C_4$alkyl$)SO_x$, $(C_1$-$C_4$haloalkyl$)SO_x$, $NO_2$ or CN groups, or phenoxy unsubstituted or substituted by one to three halogen, $C_1$-$C_4$alkyl, $C_1$-$C_4$haloalkyl, $C_1$-$C_4$alkoxy, $C_1$-$C_4$haloalkoxy, $(C_1$-$C_4$alkyl$)SO_x$, $(C_1$-$C_4$haloalkyl$)SO_x$, $NO_2$ or CN groups;

$C_3-C_{12}$cycloalkyl unsubstituted or substituted by one or more halogens, $C_1-C_6$alkyl, $C_1-C_4$haloalkyl, $C_1C_4$alkoxy, $C_1-C_4$haloalkoxy, $(C_1-C_4$alkyl$)SO_x$, $(C_1-C_4$haloalkyl$)SO_x$, phenyl unsubstituted or substituted by one to three halogen, $C_1-C_4$alkyl $C_1-C_4$haloalkyl, $C_1-C_4$alkoxy, $C_1-C_4$haloalkoxy, $NO_2$ or CN groups, or phenoxy unsubstituted or substituted by one to three halogen, $C_1-C_4$alkyl, $C_1-C_4$haloalkyl, $C_1-C_4$alkoxy, $C_1-C_4$haloalkoxy, $NO_2$ or CN groups; or phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups with the proviso that when R is phenyl, then m must be 1 or 2;

$R_1$ is hydrogen; $C_1-C_{10}$alkyl unsubstituted or substituted by one or more halogen, hydroxy, $C_1-C_4$alkoxy, $C_1-C_4$haloalkoxy, $(C_1-C_4$alkyl$)SO_x$, $CONR_6R_7$, $R_9$, $R_{10}$, $C_3-C_6$cycloalkyl unsubstituted or substituted by one to three halogen, $C_1-C_4$alkyl, $C_1C_4$haloalkyl, $C_1-C_4$alkoxy, $C_1-C_4$haloalkoxy, $NO_2$ or CN groups, phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups, or pyridyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups;

$C_2-C_{10}$alkenyl unsubstituted or substituted by one or more halogen, hydroxy, $C_1-C_4$alkoxy, $(C_1-C_4$alkyl$)SO_x$, $CONR_6R_7$, $CO_2R_8$, $R_9$, $R_{10}$, $C_3-C_6$cycloalkyl unsubstituted or substituted by one to three halogen, $C_1-C_4$alkyl, $C_1-C_4$halo-alkyl, $C_1-C_4$alkoxy, $C_1-C_4$haloalkoxy, $NO_2$ or CN groups, phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups, or pyridyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups;

$C_2-C_{10}$alkynyl unsubstituted or substituted by one or more halogen, hydroxy, $C_1-C_4$alkoxy, $(C_1-C_4$alkyl$)SO_x$, $CONR_6R_7$, $CO_2R_8$, $R_9$, $R_{10}$, $C_3-C_6$cycloalkyl one to three halogen, $C_1-C_4$alkyl, $C_1-C_4$haloalkyl, $C_1-C_4$alkoxy, $C_1-C_4$haloalkoxy, $NO_2$ or CN groups, phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups, or pyridyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups; or $C_3-C_{12}$cycloalkyl unsubstituted or substituted by one or more halogen, hydroxy, $C_1-C_4$alkoxy, $(C_1-C_4$alkyl$)SO_x$, $CONR_6R_7$, $CO_2R_8$, $R_9$, $R_{10}$, $C_3-C_6$cycloalkyl unsubstituted or substituted by one to three halogen, $C_1-C_4$alkyl, $C_1-C_4$haloalkyl, $C_1-C_4$alkoxy, $C_1-C_4$haloalkoxy, $NO_2$ or CN groups, phenyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups, or pyridyl unsubstituted or substituted by one or more halogen, $C_1-C_4$alkyl, $C_1-C_4$haloalkyl, $C_1-C_4$alkoxy, $C_1-C_4$haloalkoxy, $NO_2$ or CN groups;

$R_2$ is hydrogen or $C_1-C_4$alkyl;

$R_3$, $R_4$ and $R_5$ are each independently hydrogen, halogen, CN, $NO_2$, $(C_1-C_4$alkyl$)SO_x$, $(C_1-C_4$haloalkyl$)SO_x$, $C_1-C_6$alkyl, $C_1-C_6$haloalkyl, $C_1-C_6$alkoxy or $C_1-C_6$haloalkoxy;

$R_6$, $R_7$ and $R_8$ are each independently hydrogen or $C_1-C_4$alkyl;

$R_9$ is $NR_{11}R_{12}$,

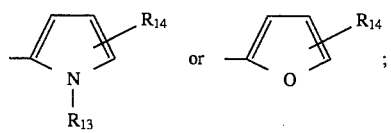

$R_{10}$ is

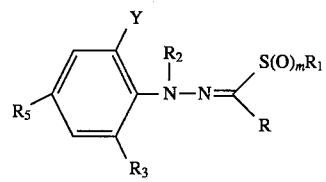

$R_{11}$, $R_{12}$, $R_{13}$ and $R_{14}$ are each independently hydrogen or $C_1-C_4$alkyl;

X is O, S or $NR_{13}$;

r is an integer of 0 or 1;

p and q are each independently an integer of 0, 1, 2, or 3 with the proviso the sum of p+q+r must be 4, 5 or 6;

x is an integer of 0, 1 or 2; or the acid addition salts thereof.

15. The compound according to claim 14 having the structure

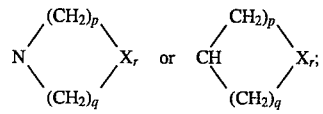

wherein

R is $C_1-C_{10}$alkyl unsubstituted or substituted by one or more halogen atoms or $C_3-C_6$cycloalkyl unsubstituted or substituted by one or more halogen or $C_1-C_4$alkyl groups; and $R_1$ is $C_1-C_{10}$alkyl unsubstituted or substituted by one or more halogen or phenyl groups, $C_2-C_{10}$alkenyl unsubstituted or substituted by one or more halogen atoms or phenyl unsubstituted or substituted by one or more halogen atoms.

16. The compound according to claim 14 wherein m is 1 or 2.

17. The compound according to claim 15 wherein m is 1 or 2.

18. The compound according to claim 15 S-ethyl-2,2-dimethylthiopropionate, 2-(2,6-dichloro-α,α,α-trifluoro-p-tolyl(hydrazone; the S-oxide thereof; the S,S-dioxide thereof or their acid addition salts.

19. A composition for controlling insect or acarid pests which comprises an inert liquid or solid carrier and a pesticidally effective amount of a compound having a structure

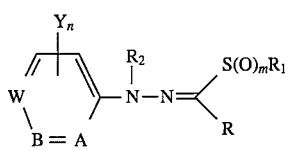

wherein A, B, W, Y, n, R, $R_1$, $R_2$, and m are described in claim 14.

20. A process for the preparation of a compound of formula Ia

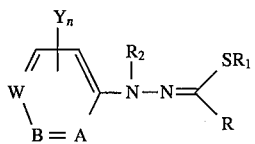
(Ia)

wherein A, B, W, Y, n, R, $R_1$, and $R_2$ are described in claim 14 which comprises reacting a compound of formula II

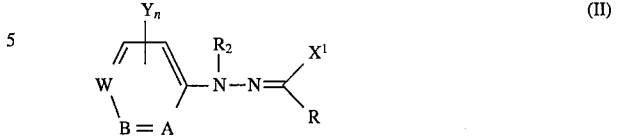
(II)

wherein $X^1$ is halogen with at least one molar equivalent of a mercaptan of formula III $$HS\text{-}R_1 \qquad (III)$$

in the presence of a base in the presence or absence of a solvent.

* * * * *